US009517033B2

(12) United States Patent
Kassai

(10) Patent No.: US 9,517,033 B2
(45) Date of Patent: Dec. 13, 2016

(54) MAGNETIC RESONANCE IMAGING APPARATUS

(71) Applicants: KABUSHIKI KAISHA TOSHIBA, Minato-ku, Tokyo (JP); TOSHIBA MEDICAL SYSTEMS CORPORATION, Otawara-shi, Tochigi (JP)

(72) Inventor: Yoshimori Kassai, Nasushiobara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 0 days.

(21) Appl. No.: 13/987,644

(22) Filed: Aug. 19, 2013

(65) Prior Publication Data

US 2013/0338487 A1 Dec. 19, 2013

Related U.S. Application Data

(60) Division of application No. 13/040,326, filed on Mar. 4, 2011, which is a continuation of application No. PCT/JP2009/065526, filed on Sep. 4, 2009.

(30) Foreign Application Priority Data

Sep. 4, 2008 (JP) .................................. 2008-226872

(51) Int. Cl.
*A61B 5/05* (2006.01)
*A61B 5/00* (2006.01)
(Continued)

(52) U.S. Cl.
CPC ............. *A61B 5/7285* (2013.01); *A61B 5/055* (2013.01); *A61B 5/7207* (2013.01);
(Continued)

(58) Field of Classification Search
CPC ................... A61B 2576/023; A61B 2576/026
USPC .................................................. 600/407–410
See application file for complete search history.

(56) References Cited

U.S. PATENT DOCUMENTS 6,252,403 B1 * 6/2001 Alsop .......................... 324/318
6,564,080 B1 * 5/2003 Kimura ........................ 600/410
(Continued)

FOREIGN PATENT DOCUMENTS

JP    2000-126156    5/2000
JP    2001-252263    9/2001
(Continued)

OTHER PUBLICATIONS

Guttman et al (Interventional cardiovascular procedures guided by real time MR imaging: An iterative interface using multiple slices adaptive projection modes and live 3D renderings, Dec. 2007).*
(Continued)

*Primary Examiner* — Joel F Brutus
(74) *Attorney, Agent, or Firm* — Nixon & Vanderhye P.C.

(57) ABSTRACT

A magnetic resonance imaging apparatus performs myocardial perfusion imaging of an object. An imaging unit acquires image data by imaging a heart of the object in synchronism with a biological signal from the object. An image generating unit generates an image concerning the heart of the object based on the image data. The imaging unit applies a probe pulse for detecting body motion of the object before imaging of the heart, and applies a spatial non-selective saturation pulse before application of the probe pulse, and a local selective pulse for flipping back a flip angle of the spatial non-selective saturation pulse with regard to a region to which the probe pulse is applied.

18 Claims, 12 Drawing Sheets

(51) Int. Cl.
*A61B 5/055* (2006.01)
*G01R 33/567* (2006.01)
*G01R 33/48* (2006.01)
*G01R 33/483* (2006.01)
*G01R 33/56* (2006.01)
*G01R 33/561* (2006.01)
*G01R 33/563* (2006.01)
*G01R 33/565* (2006.01)

(52) U.S. Cl.
CPC ..... *G01R 33/5673* (2013.01); *G01R 33/5676* (2013.01); *G01R 33/56366* (2013.01); *G01R 33/4828* (2013.01); *G01R 33/4838* (2013.01); *G01R 33/5607* (2013.01); *G01R 33/5613* (2013.01); *G01R 33/56333* (2013.01); *G01R 33/56509* (2013.01)

(56) References Cited

U.S. PATENT DOCUMENTS

| | | |
|---|---|---|
| 6,721,589 B1 | 4/2004 | Zhu et al. |
| 6,850,793 B1 | 2/2005 | Miyazaki et al. |
| 2001/0018559 A1* | 8/2001 | Itagaki et al. ............. 600/413 |
| 2003/0171671 A1* | 9/2003 | Miyazaki ................. 600/420 |
| 2005/0065430 A1 | 3/2005 | Wiethoff et al. |
| 2007/0038069 A1 | 2/2007 | Itagaki et al. |
| 2007/0083105 A1* | 4/2007 | Miyazaki et al. ......... 600/410 |

FOREIGN PATENT DOCUMENTS

| | | |
|---|---|---|
| JP | 2004-329269 | 11/2004 |
| JP | 2007-190114 | 8/2007 |
| JP | 2007-330520 | 12/2007 |

OTHER PUBLICATIONS

English translation of International Preliminary Report on Patentability in PCT/JP2009/065526 mailed Apr. 21, 2011.

International Search Report for PCT/JP2009/065526 mailed Oct. 13, 2009.

* cited by examiner

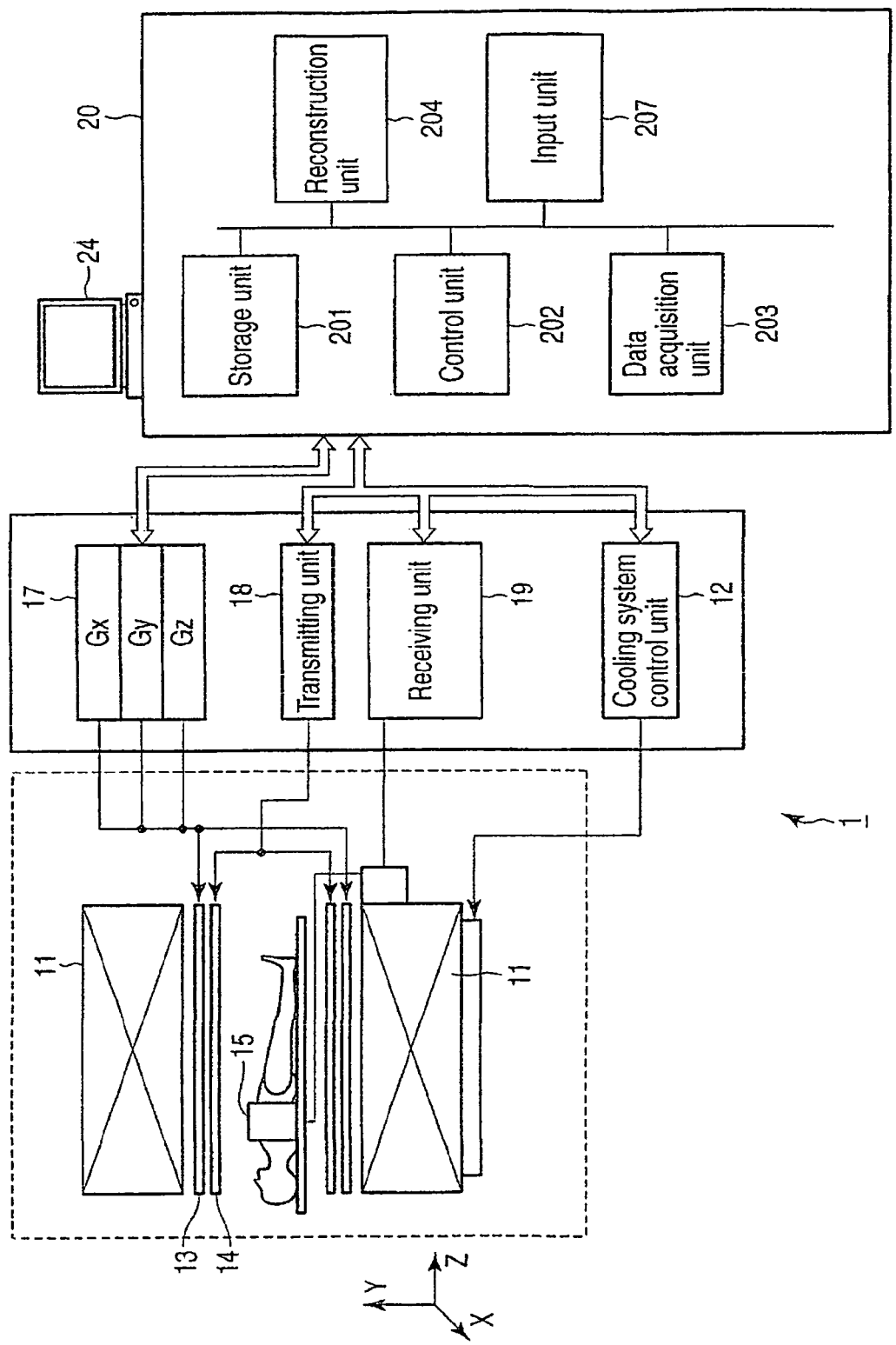
F I G. 1

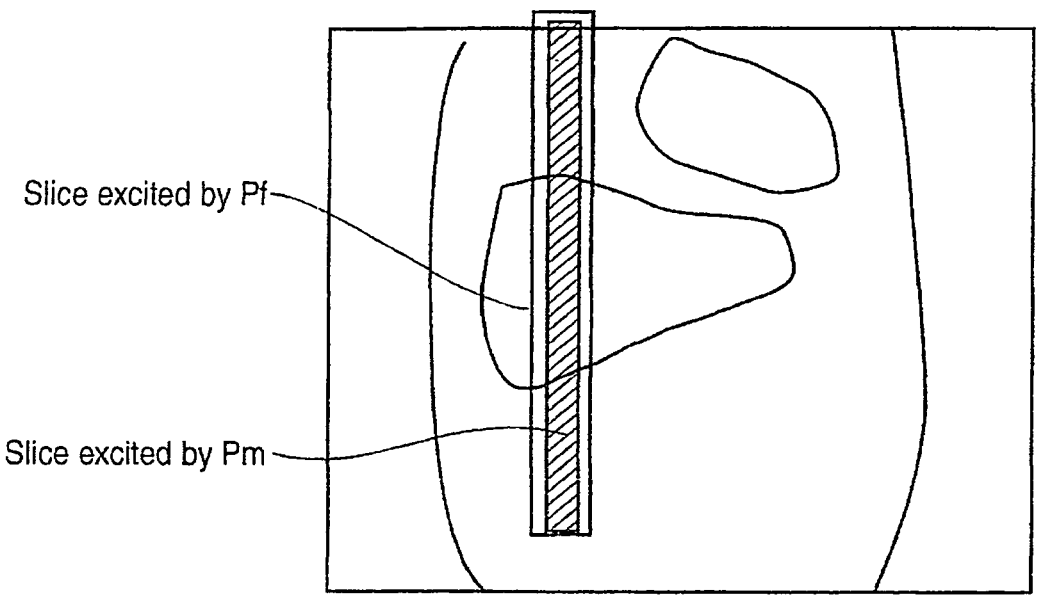
F I G. 4
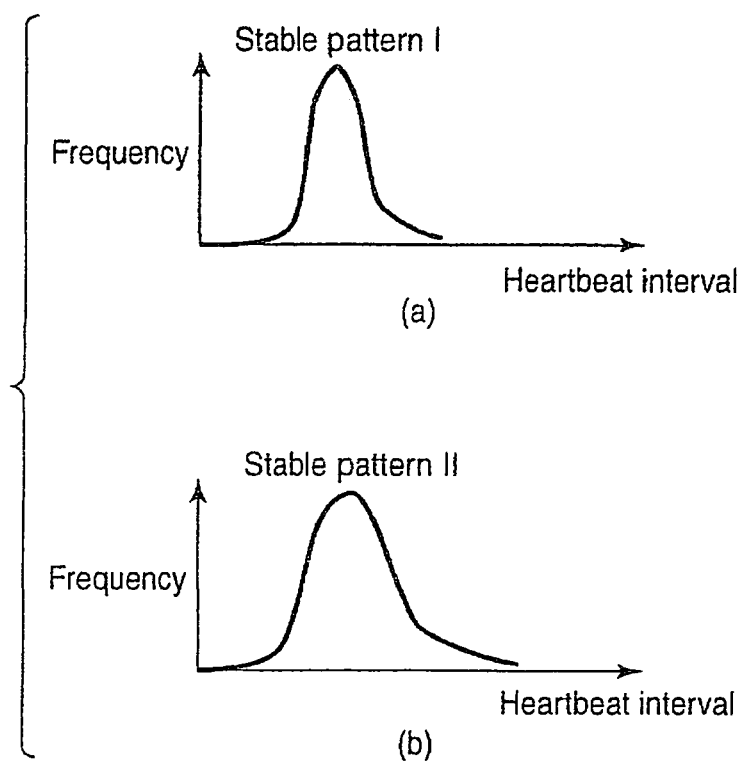
F I G. 5

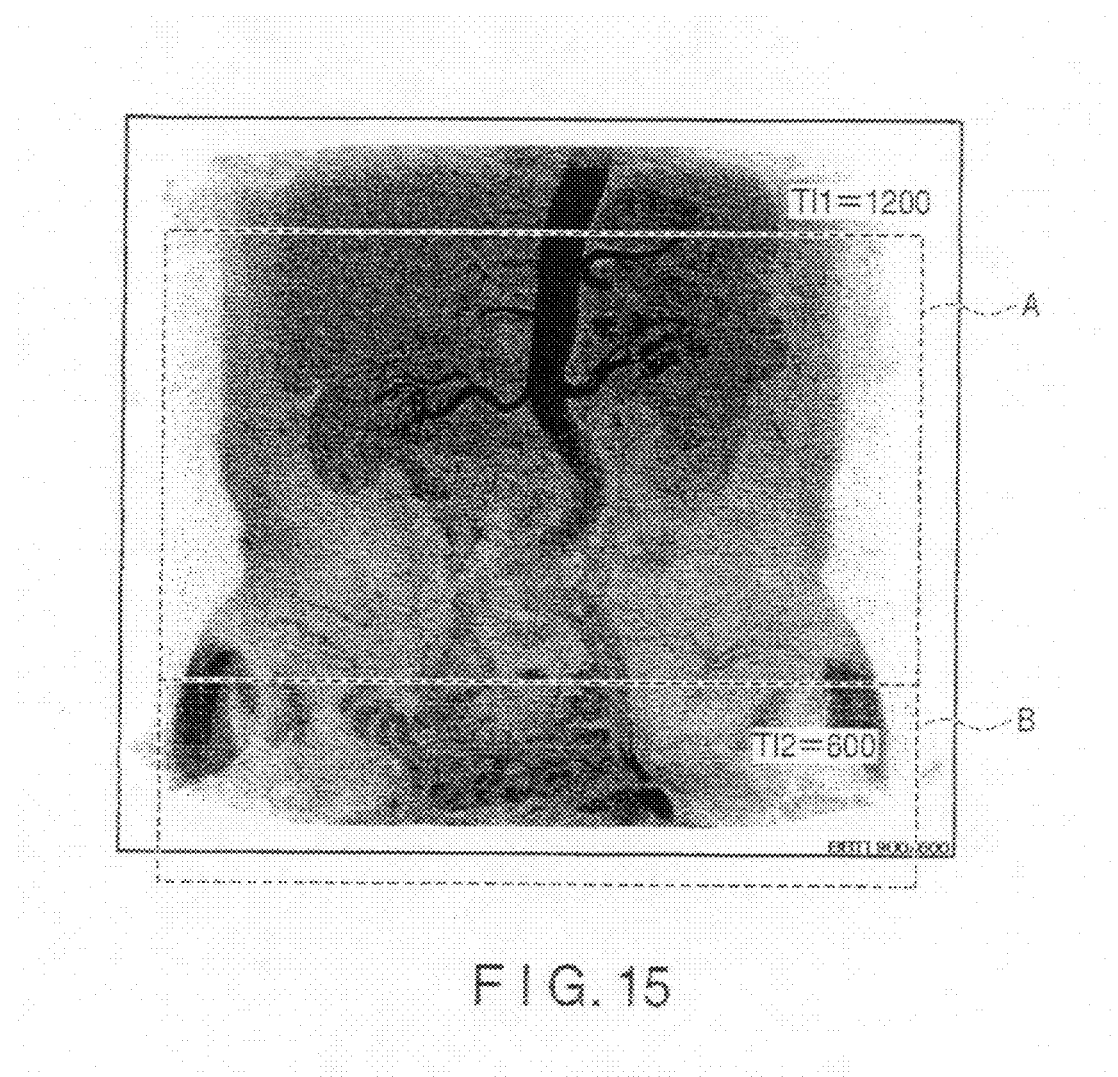
F I G. 15

MAGNETIC RESONANCE IMAGING APPARATUS

CROSS-REFERENCE TO RELATED APPLICATIONS

This is a division of co-pending U.S. Ser. No. 13/040,326 filed Mar. 4, 2011, which is a continuation of International Application No. PCT/JP 2009/065526 filed Sep. 4, 2009, which was published under PCT Article 21(2) in Japanese, and which claims priorty based on Japanese Patent Application No. 2008-226872 filed Sep. 4, 2008 the entire contents of all which are incorporated herein by reference.

FIELD

Embodiments described herein relate generally to a magnetic resonance imaging apparatus that can perform accurate myocardial perfusion imaging and non-contrast enhanced MRA, and improve cardiac diagnostic performance.

BACKGROUND

A magnetic resonance imaging apparatus is an apparatus that images the chemical and physical microscopic information of a substance or observes a chemical shift spectrum by using a phenomenon in which, when a group of nuclei having a unique magnetic moment is placed in a uniform static field, they resonantly absorb the energy of a radio-frequency magnetic field that rotates at a specific frequency. Such a magnetic resonance imaging apparatus is very effective as a method of non-invasively obtaining an image of an anatomical slice of a human body. In particular, this apparatus is widely used as a diagnosis apparatus for a central nervous system such as the brain surrounded by the skull. On the other hand, the apparatus requires a long imaging time. It is, therefore, thought that there is room for improvement in diagnostic performance for a moving organ such as the heart.

Recently, a combination of an improvement in hardware around a gradient field system and high-speed scanning has increased the number of cases in which the magnetic resonance imaging apparatus can be used for cardiac examination. Myocardial perfusion imaging, in particular, is an imaging method that can image myocardial viability in the form of the progress of staining by a contrast medium by combining an ECG gate after the injection of the contrast medium and dynamic imaging. This method has attracted a great deal of attention as an examination method that can obtain effects that cannot be obtained by other diagnosis apparatuses.

When, however, cardiac examination is to be performed by using a magnetic resonance imaging apparatus, the following problems arise.

First of all, when the heart is to be imaged on a slice basis, it is possible to obtain an image with less influence of motion by high-speed imaging such as EPI (Echo Planar Imaging). When viewed in the phase direction of dynamic imaging, an image with motion artifacts is often obtained due to respiratory body motion, a cardiac phase shift, and the like.

One solution to prevent respiratory body motion is to make a patient (object) hold his/her breath. However, making a patient with a cardiac problem hold his/her breath will undesirably increase the examination load. In addition, heartbeats may change before and after breath holding.

Further, recently, a technique called non-contrast enhanced MRA has been developed in magnetic resonance imaging. This technique images blood vessels without using a contrast medium. However, if non-contrast enhanced MRA is performed by utilizing biological information (for example, respiratory period), the following problem may occur. That is, for example, when the respiratory period of a patient becomes extremely short, the imaging is carried out even in the state where the magnetization is not fully recovered.

Embodiments have been made in consideration of the above situation, and have as their object to provide a magnetic resonance imaging apparatus that can execute accurate myocardial perfusion imaging and non-contrast enhanced MRA without requiring breath holding by a patient by making a phase of dynamic imaging relatively correspond to a cardiac phase.

BRIEF DESCRIPTION OF THE DRAWINGS

FIG. 1 is a block diagram showing the arrangement of a magnetic resonance imaging apparatus 1 according to an embodiment;

FIG. 4 is a view showing an example of a region to which the local flip-back pulse Pf and the motion probe pulse Pm are applied;

FIG. 5 is a graph each showing an example of a heartbeat pattern;

FIG. 15 is a view showing another example of a tag region set in an imaging region.

DETAILED DESCRIPTION

Figure 2:
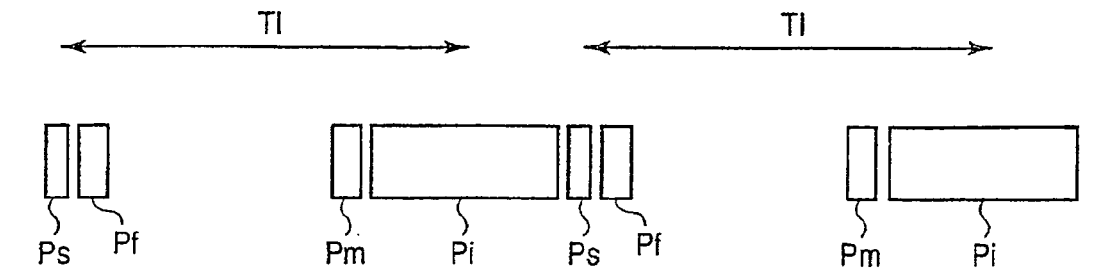
FIG. 2 is a view showing a typical example of a scan sequence executed in cardiac examination using a cardiac examination support function according to this embodiment.

In general, according to one embodiment, a magnetic resonance imaging apparatus that performs myocardial perfusion imaging of an object, the apparatus comprises an imaging unit that acquires image data by imaging a heart of the object in synchronism with a biological signal from the object, and an image generating unit that generates an image concerning the heart of the object based on the image data, wherein the imaging unit applies a probe pulse for detecting body motion of the object before imaging of the heart, and applies a spatial non-selective saturation pulse before application of the probe pulse, and a local selective pulse for flipping back a flip angle of the spatial non-selective saturation pulse with regard to a region to which the probe pulse is applied.

Embodiments will be described below with reference to the views of the accompanying drawing. Note that the same reference numerals in the following description denote constituent elements having almost the same functions and arrangements, and a repetitive description will be made only when required.

FIG. 1 is a block diagram showing the arrangement of a magnetic resonance imaging apparatus 1 according to this embodiment. As shown in FIG. 1, the magnetic resonance imaging apparatus 1 includes a static field magnet 11, a cooling system control unit 12, a gradient field coil 13, a radio-frequency transmission coil 14, a radio-frequency reception coil 15, a transmitting unit 18, a receiving unit 19, a data processing unit 20, and a display unit 24.

The static field magnet 11 is a magnet that generates a static field. This magnet generates a uniform static field.

The cooling system control unit 12 controls a cooling mechanism for the static field magnet 11.

The gradient field coil 13 is provided inside the static field magnet 11 and is shorter than the static field magnet 11. The gradient field coil 13 converts pulse currents supplied from a gradient field coil device power supply 17 into gradient fields. A signal generation region (position) is specified by the gradient fields generated by the gradient field coil 13.

Assume that the Z-axis direction is set to be the same direction as that of a static field in this embodiment. Assume also that in this embodiment, the gradient field coil 13 and the static field magnet 11 have cylindrical shapes. The gradient field coil 13 may be placed in a vacuum by a predetermined support mechanism. This arrangement is made in consideration of low noise to prevent the vibrations of the gradient field coil 13 that are generated upon application of pulse currents from being transmitted as sound waves to the outside.

The radio-frequency transmission coil (RF transmission coil) 14 is a coil for applying radio-frequency pulses to an imaging region of an object to generate magnetic resonance signals. The radio-frequency transmission coil 14 is a whole-body RF coil, which can also be used as a reception coil when, for example, an abdominal region or the like is to be imaged.

A radio-frequency reception coil (RF reception coil) 15 is a coil that is placed near the object, and preferably in contact with the object so as to hold it, and receives magnetic resonance signals from the object. In general, the radio-frequency reception coil 15 has a shape specialized for each region.

Note that FIG. 1 has exemplified a cross-coil system including a radio-frequency transmission coil and a radio-frequency reception coil as discrete components. However, the present embodiments may use a single coil system including one coil having these functions.

The gradient field coil device power supply 17 generates a pulse current for forming a gradient field and supplies the current to the gradient field coil 13. The gradient field coil device power supply 17 controls the polarity of a gradient field by switching the direction of a pulse current supplied to the gradient field coil 13 under the control of a control unit 202 (to be described later).

The transmitting unit 18 includes an oscillating unit, phase selecting unit, frequency conversion unit, amplitude modulating unit, and radio-frequency power amplifying unit (none of which are shown), and transmits radio-frequency pulses corresponding to a Larmor frequency to the radio-frequency coil for transmission. The magnetization of a predetermined nucleus of the object is excited by the radio-frequency wave generated by the radio-frequency transmission coil 14 upon this transmission.

The receiving unit 19 includes an amplifying unit, intermediate frequency conversion unit, phase detecting unit, filter, and A/D converter (none of which are shown). The receiving unit 19 performs amplification processing, intermediate frequency conversion processing using an oscillation frequency, phase detection processing, filter processing, and A/D conversion processing for the magnetic resonance signal (radio-frequency signal) that is emitted when the magnetization of the nucleus relaxes from the excited state to the ground state and is received from the radio-frequency transmission coil 14.

The display unit 24 displays a magnetic resonance image, a predetermined scan screen, and the like.

The data processing unit 20 is a computer system that generates a magnetic resonance image by processing received data, and includes a storage unit 201, the control unit 202, a data acquisition unit 203, a reconstruction unit 204, a signal correction unit 205, and an input unit 207.

The storage unit 201 stores acquired magnetic resonance images, programs for executing various scan sequences (e.g., a scan sequence for executing RMC (Real-time Motion Correction)), a dedicated program for implementing the cardiac examination support function (to be described later), and the like. In this case, RMC is a technique of monitoring a moving region such as the diaphragm and imaging the region in real time in synchronism with the motion of the region.

The control unit 202 includes a CPU and a memory (none of which are shown), and serves as a control center for the overall system to statically or dynamically control this magnetic resonance imaging apparatus. In particular, the control unit 202 implements the cardiac examination support function (to be described later) by loading the dedicated program into the memory.

The data acquisition unit 203 acquires the digital signals sampled by the receiving unit 19.

The reconstruction unit 204 executes post-processing, i.e., reconstruction such as a Fourier transform, for the data acquired by the data acquisition unit 203 to obtain the spectrum data or image data of a desired nuclear spin inside the object.

The input unit 207 includes input devices (a mouse, trackball, mode switch, keyboard, and the like) for inputting various commands, instruction, and information from the operator.

The display unit 24 is an output unit to display spectrum data, image data, or the like input from the data processing unit 20.

(Cardiac Examination Support Function)

The cardiac examination support function of the magnetic resonance imaging apparatus 1 will be described next. This function is configured to support myocardial perfusion imaging by performing spatial adjustment processing and temporal adjustment processing. In spatial adjustment, this function detects a positional shift (positional displacement amount) in the dynamic phase direction due to respiratory body motion by using, for example, RMC, and makes the slice excitation position and data acquisition position in a pulse sequence follow up the positional displacement amount, thereby suppressing the influence of the body motion. This eliminates the necessity of breath holding for stopping respiratory body motion, and hence can reduce variations in heartbeat accompanying breath holding. In temporal adjustment processing, this function measures the amount of variation in cardiac phase (temporal variation amount) due to arrhythmia or the like and adjusts various imaging conditions in accordance with the temporal variation amount. This can prevent the generation of non-analyzable data due to fluctuations in cardiac phase.

[Spatial Adjustment Processing]

FIG. 2 is a view showing a typical example of a scan sequence executed in cardiac examination using this cardiac examination support function. Referring to FIG. 2, reference symbol Ps denotes a non-selective saturation pulse (a preliminary pulse for generating contrast); Pf, a local flip-back pulse; Pm, a motion probe pulse for monitoring the body motion of a patient; and Pi, (diagnosis image) imaging pulse.

As shown in FIG. 2, in this scan sequence, constant TI is secured for the saturation pulse Ps. This is because a wait time of, for example, about TI=100 ms to 150 ms with regard to a saturation pulse is indispensable to the stabilization of contrast and images. Assume that the saturation pulse Ps is a non-selective pulse that selects no limited space to be excited. This is because, since a notched pulse like that used in, for example, Jpn. Pat. Appln. KOKAI Publication No. 2000-126156 is influenced by the inflow of blood from a notch portion from the viewpoint of image quality, making a saturation pulse non-selective can stabilize image quality.

Figure 3:
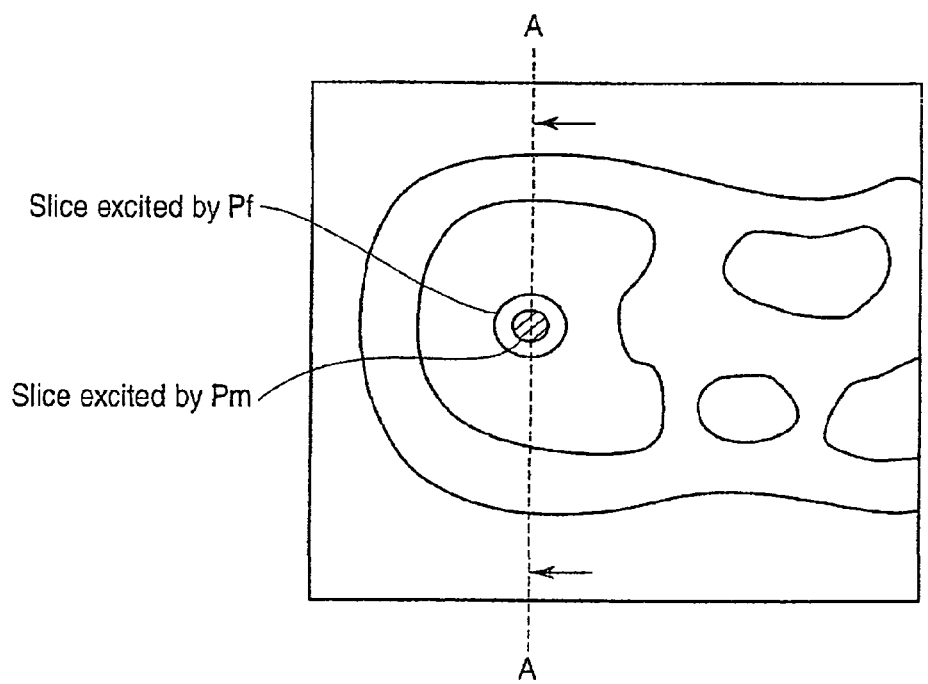
FIG. 3 is a view showing an example of a region to which a local flip-back pulse Pf and a motion probe pulse Pm are applied.

The local flip-back pulse Pf is applied immediately after the (spatially) non-selective saturation pulse Ps is applied. That is, no signal can be obtained even by applying the motion probe pulse Pm immediately after the application of the non-selective saturation pulse Ps. For this reason, the flip-back pulse Pf for recovering the magnetization of a portion to which the motion probe pulse Pm is applied is locally applied to the portion. A position detection portion (i.e., a target region to which the motion probe pulse Pm is applied) to be flipped back by the flip-back pulse Pf is a region planned to avoid the heart and large artery. This region may be a slice with a width of 2 cm to 3 cm like that shown in FIG. 3, and a local excitation pulse similar to a probe pulse may be used depending on an application. The position of the diaphragm is detected by exciting the flipped-back portion nuclei by using the motion probe pulse Pm. Assume that a region to be excited by the local flip-back pulse Pf has an area almost twice (a diameter 1.4 times) that of a region to be excited in the form of a pencil by the motion probe pulse Pm or a slice thickness about 1 to 1.5 times, as a standard value. Note that FIG. 4 is a sectional view taken along line A-A in FIG. 3 when viewed from the direction indicated by the arrow.

In addition, as shown in FIG. 2, in this scan sequence, the motion probe pulse Pm is applied during a TI wait time. If the TI wait time is required, applying a pulse for the detection of motion during the time will not degrade the imaging efficiency. In general, a pre-pulse for motion detection and correction of an imaging position are used for MRCA (Magnetic Resonance Coronary Angiography). In the case of a coronary artery, the motion of the heart in an end-diastolic period is small, and hence it is possible to correct the position of an imaging portion by correction of an imaging position. On the other hand, when imaging is to be performed in a plurality of steps (e.g., two steps), it is necessary to consider the phase difference between two steps of image acquisition. This makes it necessary to secure sufficient correction accuracy. In MRCA, therefore, it is necessary to make a contrivance not to use regions other than a predetermined region of displacement of the diaphragm for imaging. In contrast to this, in the case of myocardial perfusion imaging, applying the motion probe pulse Pm during the TI wait time can form a portion corrected by a detected diaphragm position as one image. This makes it possible to perform robust correction.

This apparatus applies the imaging pulse P1 while following up and adjusting an excited slice position (data acquisition position) so as to always excite the slice at the same position and acquire data from the slice, based on the displacement amount of a diagnosis target whose position is detected by the immediately preceding motion probe pulse Pm. Using the imaging pulse P1 upon position adjustment in this manner can image a tomogram at almost the same position. Note that it is preferable to apply a fat suppression pulse and a magnetism stabilization dummy pulse in the order named, as needed, between the motion probe pulse Pm and the imaging pulse Pi.

[Temporal Adjustment Processing]

Using the spatial adjustment processing by the cardiac examination support function can eliminate the necessity of breath holding and almost eliminate the motion of the diaphragm and the accompanying motion of the heart. It is, therefore, thought that this technique decreases the probability of variation in heartbeat as compared with the conventional imaging operation with breath holding. There is still a possibility that heartbeat may vary due to the influences of the inflow of a contrast medium and a stress medicine for the cardiac muscle. Obviously, therefore, there are needs to determine the number of slices with a margin of safety. The magnetic resonance imaging apparatus 1, therefore, can execute temporal adjustment processing capable of coping with variations in heartbeat in combination with spatial adjustment processing or singly as needed.

Note that a histogram of an average R-R interval and a heartbeat pattern are acquired before an imaging operation using this temporal adjustment processing in order to grasp how much the R-R interval of an ECG waveform is stable depending on the state of the patient. When the histogram distribution in an R-R interval has one peak, an allowable variation range of about $1.5\sigma$ or $2\sigma$ is set by using the obtained result, and a reference for R-R that is thought not to shorten any more even when a heartbeat shortens.

The following is the basic concept of this spatial adjustment processing. That is, strictness about the delay time from an ECG pulse to imaging (=cardiac phase of imaging) is not so required for myocardial perfusion imaging using FEE (Fast Field Echo) or the like, unlike cineradiography, because all data are acquired in the cardiac phase. It is, therefore, important to secure the stability of contrast between phases.

In general, gated imaging, in order to keep the time differences from electrocardiographic gates constant as much as possible, operations are basically performed as fast as possible even in the case of multi-slice imaging. Assume, however, that saturation recovery (an excitation angle of 90°) is to be used, and the spatial uniformity (B1) of RE pulses is high. In this case, there is no need to consider the history effect of longitudinal magnetization (see MRM45, 653-661, 2001), and a recovery time Tree for TI (i.e., the wait time Trec for keeping longitudinal magnetization constant) can be mainly expressed by the following equation as the function between a flip angle α of an imaging portion and TR:

$$Trec = TR/(1-\cos\alpha) \qquad (1)$$

It is, therefore, desirable to minimize the wait time between imaging slices and set TI to the value calculated from the flip angle α of imaging and TR as much as possible.

It has been confirmed from a simulation result that this condition is robust. That is, the recovery time Trec for TI need not be strict, and can be shortened in the range in which no deterioration in image quality occurs, i.e., the range of 10% to 20%. In contrast, if TI is longer than the calculated recovery time Tree for TI, a signal corresponding to first several shots will steeply attenuate. This leads to deterioration in image quality.

From the above point of view, in temporal adjustment processing by the magnetic resonance imaging apparatus 1, in order to cope with the accentuation of heart rate due to the arrhythmia of the patient or at breath holding, the apparatus measures parameters concerning a heartbeat (e.g., a histogram of an average R-R interval and a heartbeat pattern) in advance and schedules imaging in accordance with the predicted pattern of change in heartbeat of the patient.

For example, in the case of patients with heartbeats represented by stable patterns I and II shown in FIGS. 5(*a*) and 5(*b*), since an ideal state can be expected, it is possible to set Tree to a relatively long time. That is, if TR=7 ms, flip angle α=20°, and Trec=116 ms are values with which a contrast medium provides high contrast, a signal value for imaging becomes a stable condition during data acquisition.

Figure 6:
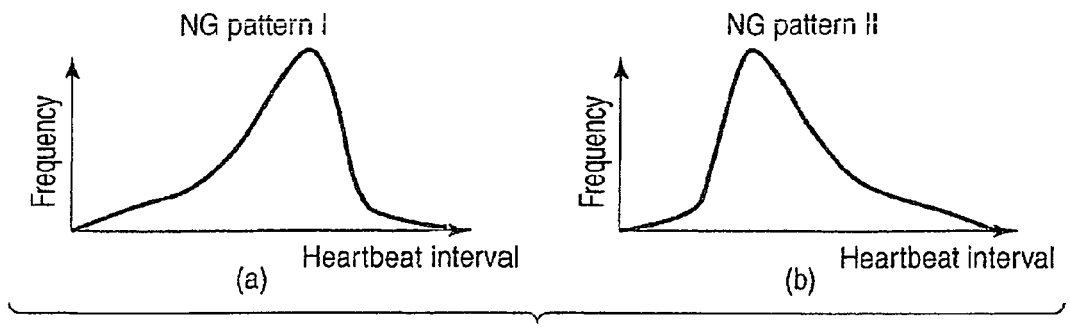
FIG. 6 is a graph each showing another example of a heartbeat pattern.
Figure 7:
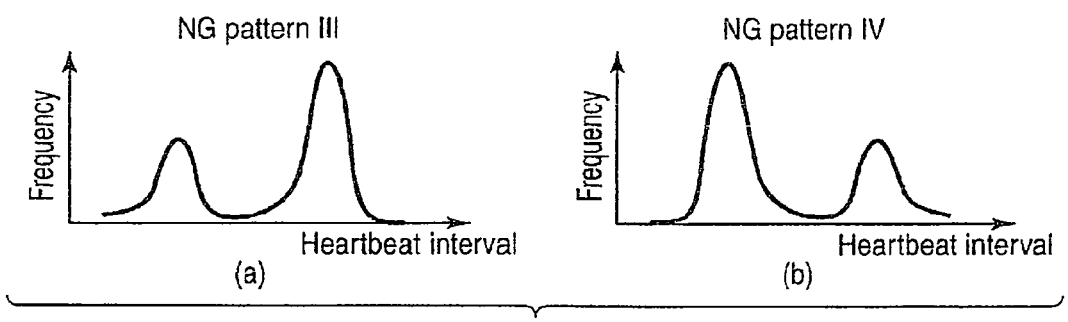
FIG. 7 is a graph each showing yet another example of a heartbeat pattern.

In the case of arrhythmia as indicated by NG patterns I and II shown in FIGS. 6(*a*) and 6(*b*) or in the case of patients simply having short pulses as represented by NG patterns I and II shown in FIGS. 7(*a*) and 7(*b*), it is important to shorten Trec, as well as adjusting the acquisition time in accordance with matrix size. In this case, for example, increasing the flip angle to α=30° will set Trec=52 ms. This can shorten the acquisition time per slice and perform stable imaging.

If it is necessary to further shorten the data acquisition time, it is possible to greatly shorten the TI time (although the effect of making TI relaxation curves between tissues uniform deteriorates) by slightly decreasing the flip angle of a saturation recovery pulse to, for example, 85°, instead of setting it to 90°.

Figure 8:
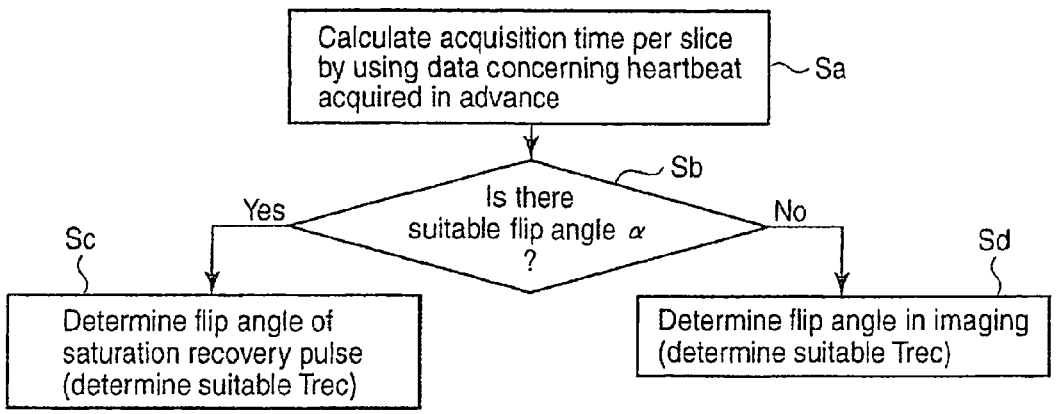
FIG. 8 is a flowchart showing a procedure for processing for scheduling dynamic imaging in accordance with a predicted pattern of change in heartbeat of a patient.

FIG. 8 is a flowchart showing a procedure for processing to be performed when dynamic imaging is scheduled in accordance with the predicted pattern of change in heartbeat of the patient. As shown in FIG. 8, first of all, the control unit 202 obtains an acquisition time per slice that allows to stably obtain a desired number of slices by using parameters concerning the heartbeat, which are acquired in advance (step Sa).

The control unit 202 then determines first the flip angle α allowing to set Trec that can guarantee sufficient image quality, within the range of flip angles α in which contrast exhibits a robust change (for example, if TR=7 ms, the range of 15° to 30° can be used as a T1 contrast image), in order to obtain conditions that satisfy the acquisition time per slice that is obtained in step Sa (step Sb).

Note that Trec has robustness, and even a change of about 10 ms to 20 ms will not abruptly degrade image quality. Therefore, the control unit 202 may calculate the desired value of Trec for each predetermined flip angle α, display the value on, for example, the monitor 24 in a predetermined form, and make the user determine a preferable combination of the flip angle α and Trec without being limited to the case in which the control unit determines the flip angle α that allows to set suitable Trec.

Upon determining in step Sb that suitable Trec cannot be sufficiently secured even if the flip angle is changed between 15° and 30°, the control unit 202 determines suitable Trec by changing the flip angle of the saturation recovery pulse Ps from the specified value, i.e., 90°, to a predetermined angle between, e.g., 80° and 85° (step Sc).

Upon determining in step Sb that suitable Trec can be sufficiently secured by setting the flip angle to a predetermined angle between 15° and 30°, the control unit 202 determines the angle as the flip angle α of imaging (step Sd).

As described above, it is possible to easily set imaging conditions allowing stable myocardial perfusion imaging by sequentially calculating and using approximate values of Trec, flip angles at the time of imaging, and flip angles at the time of saturation with regard to conditions for the imaging pulse P1 and non-selective saturation pulse Ps.

The magnetic resonance imaging apparatus 1 also has a function of readjusting the imaging conditions set by the above scheduling operation in response to, for example, the occurrence of arrhythmia during imaging.

Figure 9:
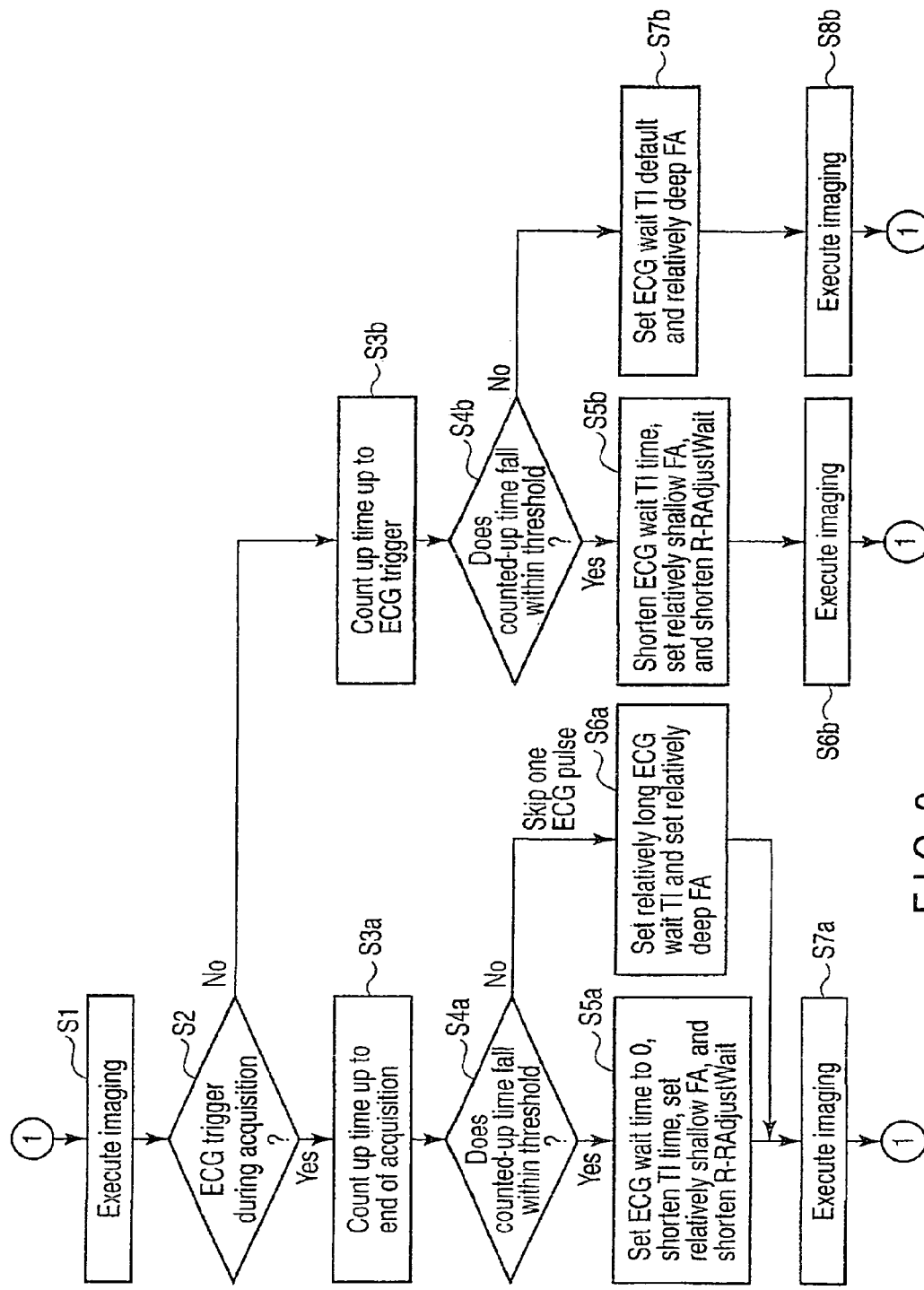
FIG. 9 is a flowchart showing a procedure for processing (imaging condition readjustment processing) conforming to an imaging condition readjustment function.

FIG. 9 is a flowchart showing a procedure for processing (imaging condition readjustment processing) conforming to the imaging condition readjustment function. As shown in FIG. 9, the control unit 202 executes imaging using imaging conditions conforming to scheduling in response to ECG as a trigger (step S1). At this time, in order to cope with predicted arrhythmia, it is preferable to set a relatively small number of slices in scheduling for imaging. The control unit 202 then determines whether an ECG trigger (e.g., an R wave) is generated during imaging (image acquisition) (step S2). Upon determining in step S2 that an EGG trigger is generated during image acquisition, the control unit 202 counts up the time up to the end of currently performed image acquisition (step S3*a*).

The control unit 202 then determines whether the time counted up in step S3*a* falls within a predetermined threshold (step S4*a*). Upon determining that the time falls within the predetermined threshold, the control unit 202 re-sets conditions for imaging in synchronism with the next EGG trigger (without any interval of heartbeat) by, for example, shortening the wait time for an ECG trigger, shortening the wait time from a saturation pulse to an imaging pulse, suppressing the flip angle of the saturation pulse, and increasing the flip angle of the imaging pulse (step S5*a*). In contrast, upon determining in step S4*a* that the time falls outside the predetermined threshold, the control unit 202 re-sets conditions for imaging in synchronism with an ECG trigger after one heartbeat (step S6*a*). The control unit 202 executes subsequent dynamic imaging by using the conditions re-set in step S5*a* or S6*a* (step S7*a*).

Upon determining in step S2 that no ECG trigger is generated during image acquisition, the control unit 202 counts up the time up to the next ECG trigger based on parameters concerning a heartbeat that are acquired in advance (step S3*b*).

The control unit 202 determines whether the time counted up in step S3*b* falls within a predetermined threshold (step S4*b*). Upon determining that the time falls within the predetermined threshold, the control unit 202 re-sets conditions that establish synchronism with the next ECG trigger (without any interval of heartbeat) and prevent the timing of image acquisition from overlapping that of the ECG trigger by, for example, shortening the wait time for an ECG trigger, shortening the wait time from a saturation pulse to an imaging pulse, suppressing the flip angle of the saturation pulse, and increasing the flip angle of the imaging pulse (step S5b). The control unit 202 executes subsequent dynamic imaging by using the re-set conditions (step S6b).

In contrast, upon determining in step S4b that the time falls outside the predetermined threshold, the control unit 202 re-sets conditions for imaging in synchronism with the next ECG trigger (without any interval of heartbeat) (step S7b). The control unit 202 executes subsequent dynamic imaging by using the re-set conditions (step S8b).

Figure 10:
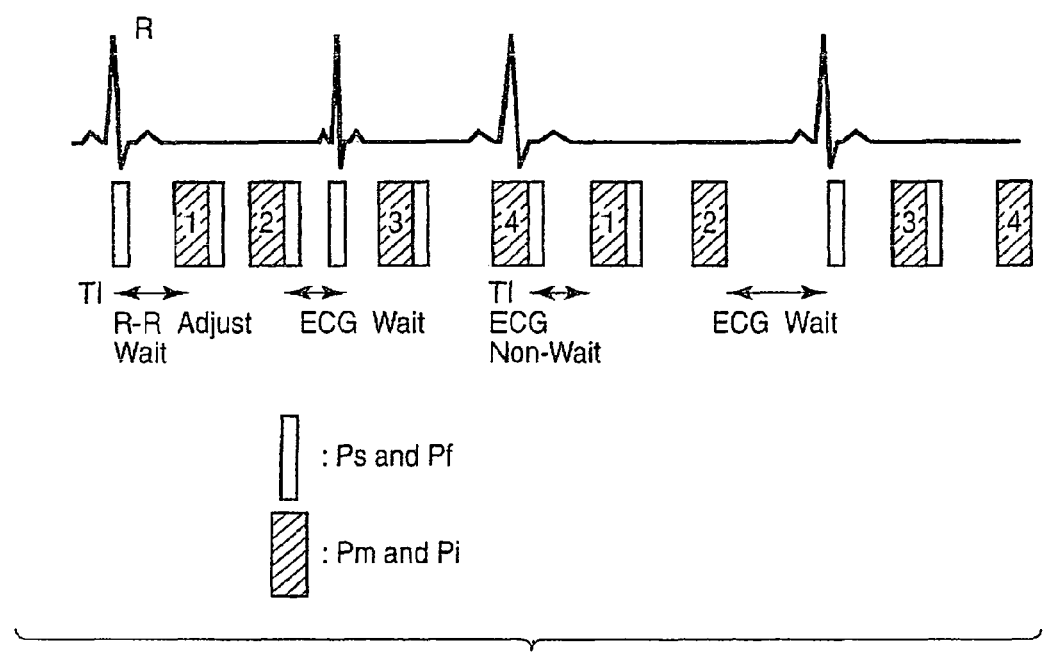
FIG. 10 is a view showing an example of a scan sequence in dynamic imaging executed by cardiac examination support processing according to this embodiment.

The control unit 202 executes the above imaging condition readjustment processing every time imaging is repeated, thus executing a series of dynamic imaging like that shown in FIG. 10. Using such an imaging condition readjustment function in addition to the first scheduling can perform imaging without any phase shift relative to a heartbeat by compensating for the delay time from the heartbeat as much as possible even if the wait time is shortened.

(Effects)

According to the above arrangement, the following effects can be obtained.

This magnetic resonance imaging apparatus detects a displacement amount in the dynamic phase direction due to respiratory body motion in myocardial perfusion imaging, and makes the slice excitation position and data acquisition position follow up the body motion based on the displacement amount. This makes it unnecessary for the patient to hold breath, and hence can reduce variations in heartbeat.

In addition, this magnetic resonance imaging apparatus measures the variation amount of a cardiac phase, and controls the wait time from a saturation pulse to an imaging pulse, the suppression of the flip angle of the saturation pulse, and the flip angle of the imaging pulse in accordance with the variation amount. This can make a phase of dynamic imaging relatively correspond to a cardiac phase and schedule imaging conditions in accordance with a heartbeat change pattern. It is, therefore, possible to correct the positional shift of a myocardial perfusion image in the dynamic phase direction due to slight respiratory body motion or variations in heartbeat.

Furthermore, this magnetic resonance imaging apparatus monitors the correspondence relationship between an ECG trigger and a phase of dynamic imaging, and can readjust set imaging conditions in real time based on the phase shift. This can improve the robustness of dynamic imaging and prevent the generation of non-analyzable data due to fluctuations in cardiac phase, thereby implementing stable myocardial perfusion imaging. Applying a feedback to a saturation pulse, in particular, can implement stable saturation even for a slice immediately after a heartbeat, from which a proper saturation effect has not been obtained. Stabilizing saturation will increase the degree of freedom relative to cardiac phases and allows use of a method of dividing a multi-slice for each R-R interval.

Second Embodiment

A magnetic resonance imaging apparatus according to the second embodiment of the present embodiments will be described next. In the magnetic resonance imaging apparatus according to this embodiment, temporal adjustment processing is applied to non-contrast enhanced MRA imaging. That is, the magnetic resonance imaging apparatus according to this embodiment acquires a non-contrast enhanced MRA image with less influence of body motion by adjusting at least one of the flip angle of an IR pulse and the flip angle of an imaging RE pulse in accordance with variations in biological signal such as a respiratory period in an interval (to be referred to as "TI" hereinafter) from the application time of an inversion recovery pulse (IR pulse) for tagging to the application time of the first RF pulse for imaging. Such a non-contrast enhanced MRA imaging method is sometimes called a Time-SLIP (Time-Spatial Labeling Inversion Pulse) method from the viewpoint that a given region of an object is temporally and spatially labeled by applying an IR pulse to it.

Note that "tagging" means that an observation target (e.g., a blood vessel of interest) is temporally and spatially labeled (tagged) in the form of longitudinal magnetization to depict an MR signal from blood or the like with high or low intensity as compared with a signal from other regions (i.e., to generate contrast). A region of an object to be tagged by applying an IR pulse (or a corresponding region on an image) is called a tag region.

IR pulses include a "spatial selective IR pulse" and a "spatial non-selective IR pulse". A "spatial selective IR pulse" is used to tag a specific space selected in an imaging region as a tag region. In contrast, a "spatial non-selective IR pulse" is used to tag an entire imaging region as a tag region instead of selecting a specific space in the imaging region. The latter can be freely turned on and off automatically depending on the type of non-contrast enhanced MRA to be selected or by predetermined operation through an input unit 207.

In temporal adjustment processing in a magnetic resonance imaging apparatus 1 according to this embodiment, in order to cope with the disturbance of the respiratory period of the patient, parameters concerning a respiratory period (e.g., a histogram of an average expiratory peak interval and a respiratory period pattern) are measured in advance, and imaging scheduling is performed in accordance with the predicted pattern of change in respiratory period of the patient. Moreover, in the actual scan operation, as monitoring respiratory period of the patient is monitored, the pulse sequence that is synchronized with the respiratory period of the patient is performed repeatedly.

It is said that a respiratory period of human is generally about 3,000 msec to 5,000 msec. If, therefore, for example, the average respiratory period is as relatively long as about 5,000 msec and stable, non-contrast enhanced MRA imaging is scheduled with TI and the flip angle of a tagging pulse being respectively set to about 1,500 msec and α=180°. In contrast, if the average respiratory period is as relatively short as about 3,000 msec, non-contrast enhanced MRA imaging is scheduled with TI being set to about 1,200 msec by adjusting the flip angle α of a tagging pulse within the range of, for example, 90°≤α≤180° or adjusting the delay time from an expiratory trigger to a tagging trigger, a matrix size, the application time of an RF pulse for imaging, and the like.

Figure 11:
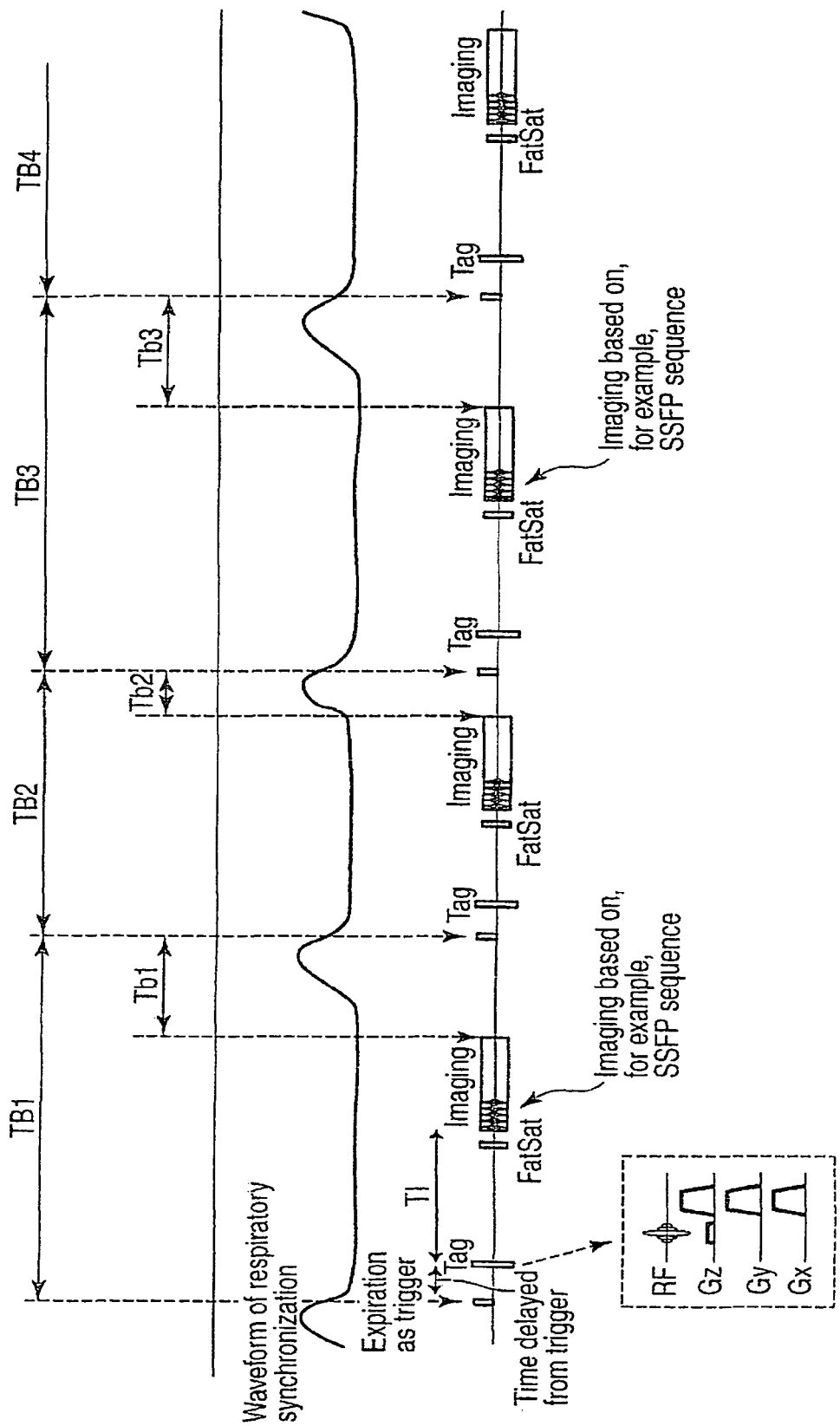
FIG. 11 is a view showing an example of a scan sequence in non-contrast enhanced MRA executed by setting a single tag region and using breath expiration as a trigger.
Figure 12:
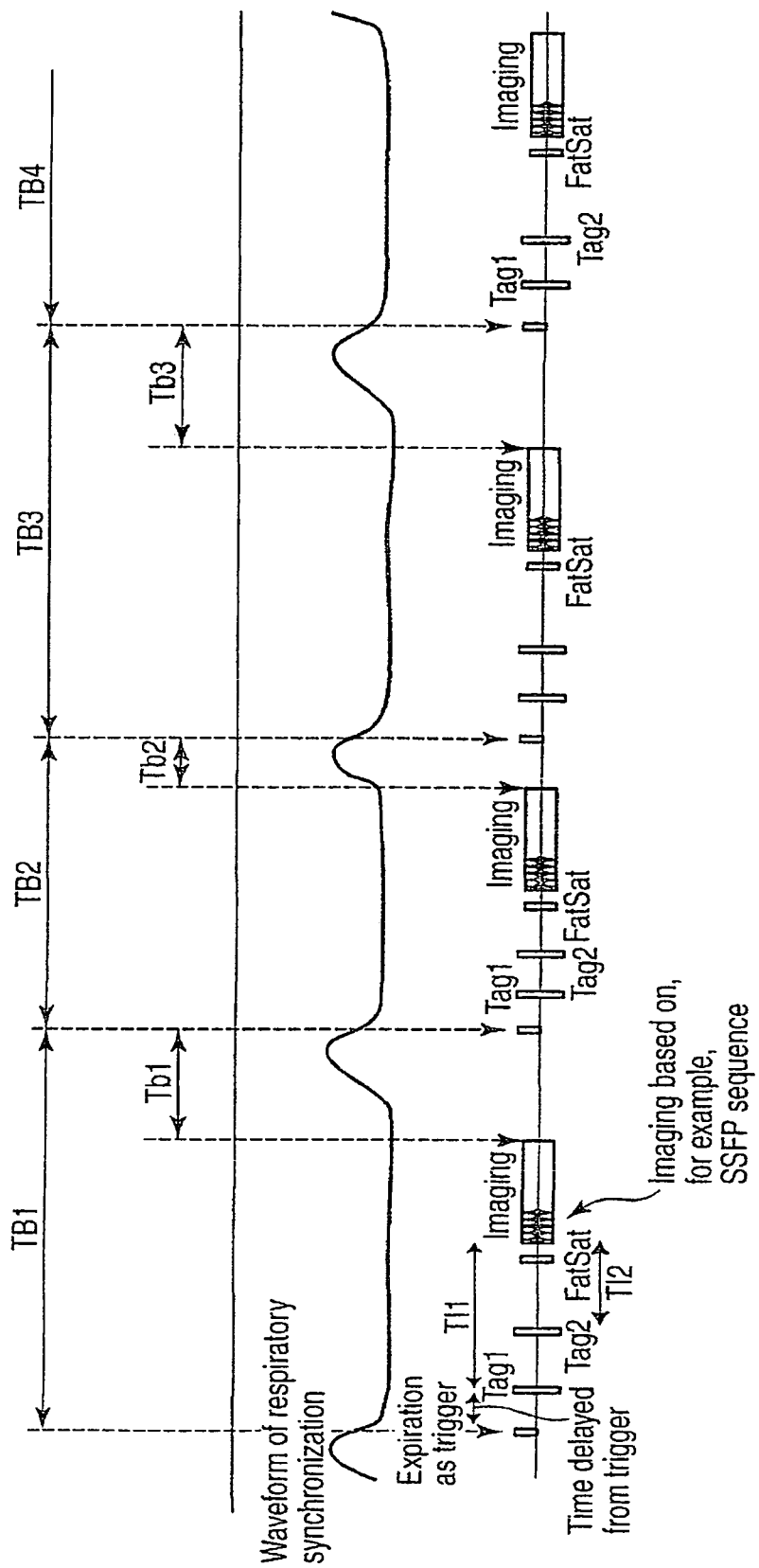
FIG. 12 is a view showing an example of a scan sequence in non-contrast enhanced MRA executed by setting a plurality of tag regions (two regions Tag1 and Tag2 in the case shown in FIG. 12) and using an expiration as a trigger.
Figure 13:
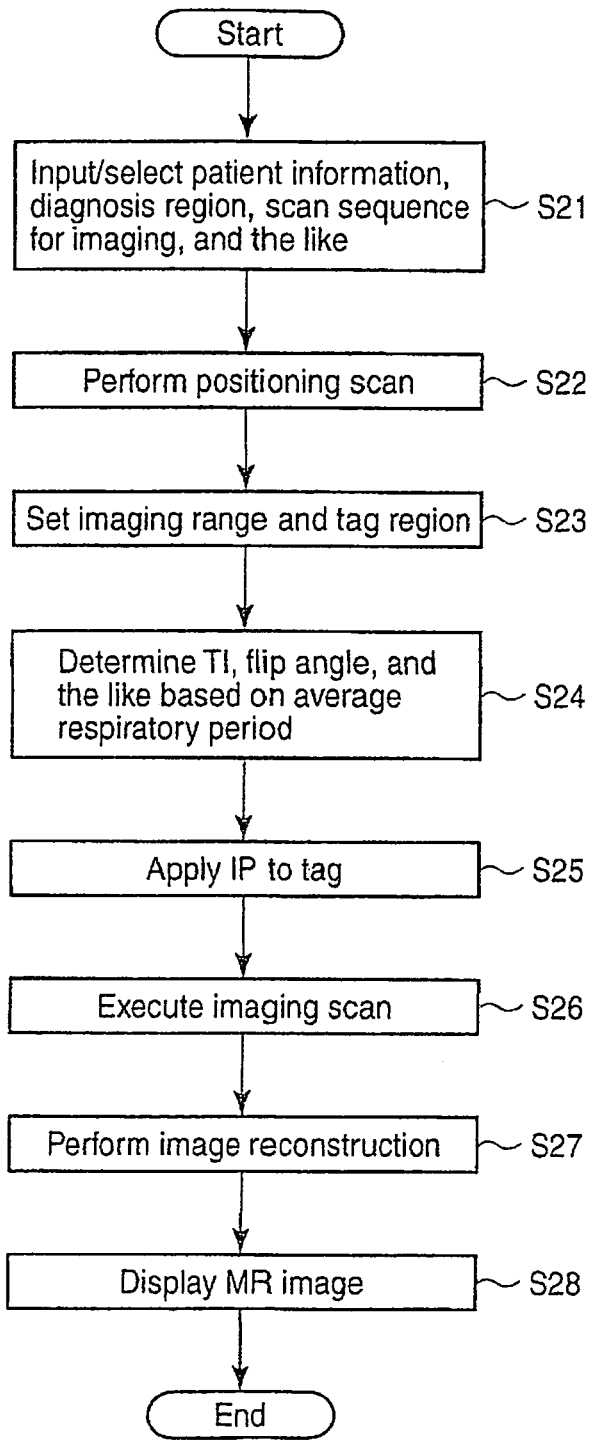
FIG. 13 is a flowchart showing a procedure for processing in non-contrast enhanced MRA imaging.

FIG. 11 is a view showing an example of a scan sequence for non-contrast enhanced MRA in a case where a single Tag region is set and a region including the renal artery of the patient is volume-scanned by using breath expiration as a trigger. FIG. 12 is a view showing an example of a scan sequence for non-contrast enhanced MRA in a case where a plurality of Tag regions (two regions Tag1 and Tag2 in the case shown in FIG. 12) is set and a region including the renal artery of the patient is volume-scanned by using breath expiration as a trigger. FIG. 13 is a flowchart showing a procedure for processing in non-contrast enhanced MRA imaging. The operation of this magnetic resonance imaging apparatus will be described with reference to the flowchart of FIG. 13 by using the sequence shown in FIG. 11 or 12. The operation can be used in a case where the volume data corresponding to a region including the renal artery of the patient is obtained by executing a scan, which is for acquiring a predetermined amount of data (for example, an amount corresponding to one slice encode) in a respiratory period, repeatedly in synchronization with respiratory motion of the patient.

As shown in FIG. 13, first of all, when patient information, a diagnosis region, a scan sequence used for imaging, and the like are input and selected through an input device 13 (step S21), a host computer 6 executes a positioning scan for acquiring a positioning image used to set an imaging range and a tag region (step S22).

Figure 14:
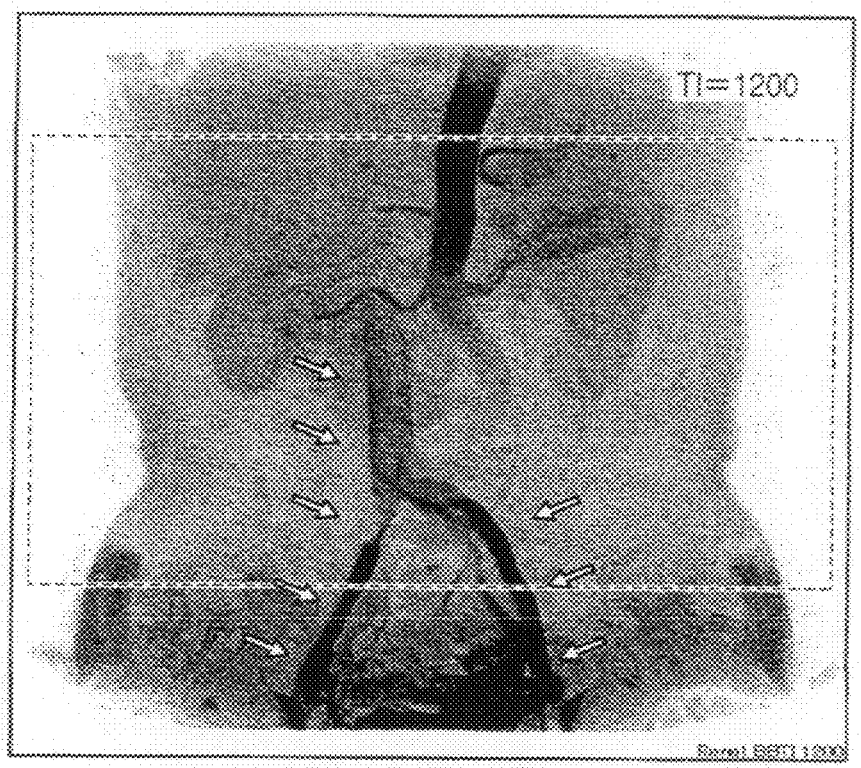
FIG. 14 is a view showing an example of a tag region set in an imaging region.

Using the acquired positioning image, the host computer 6 sets an imaging range and a tag region in accordance with inputs from the input device 13 (step S23). At this time, if, for example, a single tag region is to be set (i.e., in accordance with the scan sequence shown in FIG. 11), the host computer 6 sets an imaging range and a tag region as shown in FIG. 14. If a plurality of tag regions are to be set (i.e., in accordance with the scan sequence shown in FIG. 12), the host computer 6 sets an imaging range and a plurality of tag regions as shown in FIG. 15.

The host computer 6 then determines a flip angle $\alpha$ of a tagging pulse and Ti based on the average respiratory period (step S24). If, for example, the average respiratory period is about 3,000 msec, the host computer 6 determines flip angle $\alpha=120°$ and TI=1,200 msec in the case shown in FIGS. 11 and 14, and determines flip angle $\alpha=120°$, TI1=1,200 msec, and TI2=600 msec in the case shown in FIGS. 12 and 15.

A sequencer 5 then executes non-contrast enhanced MRA by using the set imaging range and tag region in accordance with a scan sequence. When, for example, the scan sequence in FIG. 12 is to be followed, the sequencer 5 applies the first IR pulse to a tag region A at the timing delayed from an expiratory trigger by a predetermined interval, and further applies the second IR pulse to a tag region B a predetermined interval after the application of the first IR pulse (step S25). The sequencer 5 repeatedly executes an imaging scan in accordance with a predetermined sequence an interval TI1 after the application time of the first IR pulse (or an interval TI2 after the application time of the second IR pulse) (step S26).

Note that in a scan sequence using an expiration as a trigger such as shown in FIGS. 11 and 12, an actual respiratory period sometimes becomes extremely short depending on, for example, the physical or mental condition of the patient. As a result, the flip angle $\alpha$ and TI of the tagging pulse scheduled in advance are not appropriate as they are. For example, it is such a case where while executing the scan sequence shown in FIG. 11 on a patient whose average respiratory period is about 5000 msec with a flip angle $\alpha=180°$ and TI=1200 msec in scheduling, the respiratory period TB2 suddenly shortens to, for example, about 3000 msec. In this case, the period Tb2 from the scan end time in the respiratory period TB2 to the expiration timing in the respiratory period TB3 becomes extremely short. For this reason, there may be some case where the time for restoring the magnetization cannot be fully secured with pre-scheduled flip angle $\alpha$ and TI of the tagging pulse as they are.

To acquire MR images with stable contrast pattern in this case, the magnetic resonance imaging apparatus includes the function of readjusting and the function of re-executing.

The function of readjusting executes dynamic adjustments of the flip angle $\alpha$ and TI of tagging pulse, which are determined in scheduling, with response to the variation in respiratory period during monitoring. For example, with response to the period Tb2 from the scan end time in the respiratory period TB2 to the expiration timing in the respiratory period TB3 shown in FIG. 11, appropriate flip angle $\alpha$ and TI are re-calculated and updated in real time during the time period between the expiration trigger to the application of the tagging pulse. Further, in accordance with necessity, the flip angle of RF pulse for imaging is changed. The changing of the flip angle $\alpha$ and TI described above are dynamically executed with response to a period Tbi from the scan end time in a respiratory period TBi to the expiration timing in the next respiratory period TBi+1. It should be noted that in the case where there are a plurality of Tag regions as shown in FIG. 12, the function of re-adjustment is used for the flip angle $\alpha$ and TI of each tagging pulse in each of the Tag regions.

Figure 16:
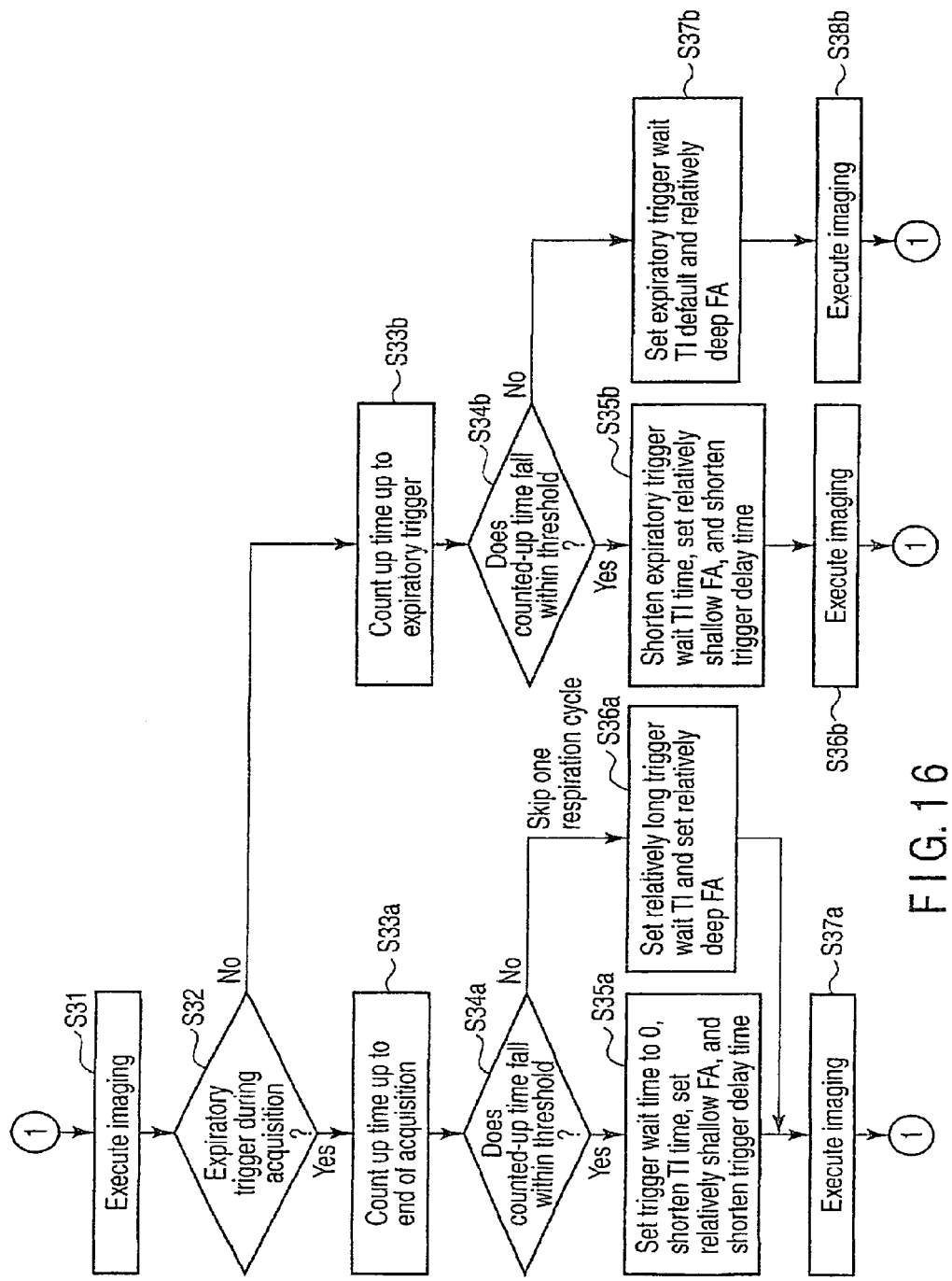
FIG. 16 is a flowchart showing a procedure for processing (imaging condition readjustment processing) conforming to the imaging condition readjustment function.

FIG. 16 is a flowchart showing a procedure for processing (imaging condition readjustment processing) conforming to the imaging condition readjustment function. As shown in FIG. 16, a control unit 202 executes imaging using imaging conditions conforming to scheduling in response to breath expiration as a trigger (step S31). At this time, in order to cope with the predicted disturbance of breath expiration, it is preferable to set a relatively small number of slices in imaging scheduling. The control unit 202 then determines whether an expiratory trigger is generated during imaging (image acquisition) (step S32). Upon determining in step S32 that an expiratory trigger is generated during image acquisition, the control unit 202 counts up the time up Lo the end of currently performed image acquisition (step S33a).

The control unit 202 then determines whether the time counted up in step S33a falls within a predetermined threshold (step S34a). Upon determining that the time falls within the predetermined threshold, the control unit 202 re-sets conditions for imaging in synchronism with the next expiratory trigger (without any interval of one respiratory cycle) by, for example, shortening the wait time for an expiratory trigger, shortening the delay time from the expiratory trigger, shortening the wait time from a tagging pulse to an imaging pulse, suppressing the flip angle of the tagging pulse, and increasing the flip angle of the imaging pulse (step S35a). In contrast, upon determining in step S34a that the time falls outside the predetermined threshold, the control unit 202 re-sets conditions for imaging in synchronism with an expiratory trigger after one respiratory cycle (step S36a). The control unit 202 executes subsequent dynamic imaging by using the conditions re-set in step S35a or S36a (step S37a).

Upon determining in step S32 that no expiratory trigger is generated during image acquisition, the control unit 202 counts up the time up to the next expiratory trigger based on parameters concerning the respiratory period acquired in advance (step S33b).

The control unit 202 determines whether the time counted up in step S33b falls within a predetermined threshold (step S34b). Upon determining that the time falls within the predetermined threshold, the control unit 202 re-sets conditions that establish synchronism with the next expiratory trigger (without any interval of one respiratory cycle) and prevent the timing of image acquisition from overlapping that of expiratory trigger by, for example, shortening the wait time for an expiratory trigger, shortening the wait time from a tagging pulse to an imaging pulse, suppressing the flip angle of the tagging pulse, and increasing the flip angle of the imaging pulse (step S35b). The control unit 202 executes subsequent dynamic imaging by using the re-set conditions (step S36b).

In contrast, upon determining in step S34b that the time falls outside the predetermined threshold, the control unit 202 re-sets conditions for imaging in synchronism with an expiratory trigger (without any interval of one respiratory cycle) (step S37b). The control unit 202 executes subsequent dynamic imaging by using the re-set conditions (step S38b).

The control unit 202 executes the above imaging condition readjustment processing every time imaging is repeated, thus executing a series of dynamic imaging. Using such an imaging condition readjustment function in addition to the first scheduling can perform imaging without any phase shift relative to a heartbeat by compensating for the delay time from the heartbeat as much as possible even if the wait time is shortened. As described above, the function of re-adjustment is very effective if the period Tbi from the scan end time in a respiratory period TBi to the expiration timing in the next respiratory period TBi+1 is a certain value or more (for example, 800 ms or more). On the other hand, in the case where the period Tbi is extremely short as, for example, 500 ms, an MR image with a stabilized contrast cannot be obtained even if the dynamic adjustment function is used. The function of re-adjustment should be used in the case where the recovery is not possible if the dynamic adjustment function is used as discussed above.

That is, the function of re-adjustment is that when the period Tbi in a respiratory period TBi is extremely snort, the data obtained in the state where the magnetization is not fully recovered in the next respiratory period TBi+1 (for example, data corresponding to the i-th slice encode) is rejected, and the scan that follows the identical encode pattern to that of the scan of the next respiratory period TBi+1 is re-executed in one of the respiratory periods from the period TBi+2 or later. It should be noted that the re-execution may be carried out in any one of these respiratory periods. As a typical example, when data is obtained in the state where the magnetization is not fully recovered in the respiratory period TBi+1, the re-execution is done in the next respiratory period TBi+2, or after executing the scanning operations of all encode patterns.

A computing unit 10 performs image reconstruction by using an MR signal obtained by imaging, and forms volume data regarding the region including the renal artery. Further, a computing unit 20 uses the volume data formed to generate an MR image regarding a desired cross section (step S27). Note that data obtained in the state where the magnetization is not fully recovered is not employed for the reconstruction of this step. A display device 12 displays the generated MR signal as a moving image or a still image (step 528).
(First Modification)

The second embodiment has exemplified the imaging sequence using the three-dimensional SSFP (Steady-State Free Precession) method (see FIGS. 11 and 12). However, the present embodiment is not limited to this. For example, it is possible to perform imaging by using other scan sequences such as a three-dimensional FSE (Fast Spin-Echo) method and a three-dimensional FASE (Fast Advances Spin-Echo) method. In addition, an image acquisition form to be used can be a single or multi-shot form. If, for example, the case in FIG. 2 is a sequence conforming to the single-shot three-dimensional SSFP method, first slice encoding is executed in imaging I, and second slice encoding is executed in subsequent imaging II. In contrast, if the case in FIGS. 11 and 12 is a sequence conforming to the multi-shot (two-shot) three-dimensional SSFP method, the first shot in first slice encoding is executed in imaging I, and the second shot in first slice encoding is executed in subsequent imaging II.

(Second Modification)

The second embodiment has exemplified the case in which a biological signal is a respiratory period. However, the present embodiment is not limited to this. For example, the technical idea of the present embodiment can also be applied to non-contrast enhanced MRA imaging using an ECG waveform or pulse waveform as a biological signal.

According to the above arrangement, this apparatus measures the variation amount of a respiratory period, and controls the wait time from a tagging pulse to an imaging pulse, the suppression of the flip angle of the tagging pulse, and the flip angle of the imaging pulse in accordance with the variation amount in non-contrast enhanced MRA imaging. This can make a phase of dynamic imaging relatively correspond to a cardiac phase and schedule imaging conditions in accordance with a respiratory period change pattern. It is, therefore, possible to correct a positional shift in the dynamic phase direction in non-contrast enhanced MRA imaging due to variations in respiratory period. Further, in the case where the actual respiratory period becomes short depending on, for example, the physical or mental conditions of the patient, the flip angle α and TI of tagging pulse, determined in scheduling are dynamically readjusted with response to the variation in respiratory period during monitoring. Furthermore, in case where the dynamic re-adjustment does not work for some reason and the data obtained in the state where the magnetization is not fully recovered, the data obtained is rejected, and the scan that follows the identical encode pattern to that of the scan of one of the later respiratory periods is re-executed. In this manner, even in the case where the respiration or the like of the patient is disturbed, a highly accurate non-contrast enhanced MRA can be realized.

Note that the present invention is not limited to each embodiment described above, and constituent elements can be modified and embodied in the execution stage within the spirit and scope of the invention. In addition, various inventions can be formed by proper combinations of a plurality of constituent elements disclosed in the above embodiments. For example, several constituent elements may be omitted from all the constituent elements disclosed in the above embodiments. Furthermore, constituent elements in different embodiments may be properly combined.

What is claimed is:

1. A magnetic resonance imaging (MRI) apparatus, comprising:
an MRI control system, connected to control gantry components, including at least one RF transmitter, at least one RF receiver and computer control circuits configured to effect specified MRI data acquisition sequences of RF and gradient magnetic pulses which acquire, from an object located within an imaging volume, RF nuclear magnetic resonance (NMR) spin responses emanating from different spatially located volumes of MRI nuclei respectively corresponding to different positions in k-space as a function of a magnetic field experienced by the nuclei;
said computer control circuits being configured to effect:
acquisition of MR image data from a predetermined region of an object by using a labeling pulse to generate contrast in the image data between different tissues and an RF pulse synchronized with a biological signal of the object which periodically fluctuates;
acquisition of a pattern of the biological signal of the object concurrent with execution of MRI data acquisition sequences;

dynamic real time adjustment of at least one image acquisition sequence condition parameter being used in said data acquisition sequences in response to a temporal change in the pattern of the biological signal; and generation of an image of tissues in the predetermined region using the acquired image data which includes tissue contrast generated by the labeling pulse.

2. The magnetic resonance imaging apparatus of claim 1, wherein a spatial nonselective pulse is used as the labeling pulse.

3. The magnetic resonance imaging apparatus of claim 1, wherein a spatial selective pulse is used as the labeling pulse.

4. The magnetic resonance imaging apparatus of claim 1, wherein a spatial selective pulse of each of a plurality of regions to be labeled is used as the labeling pulse.

5. The magnetic resonance imaging apparatus of claim 1, wherein a period between an application time of the labeling pulse and a first application time of the RF pulse is dynamically adjusted.

6. The magnetic resonance imaging apparatus of claim 1, wherein a flip angle of the labeling pulse is dynamically adjusted.

7. The magnetic resonance imaging apparatus of claim 1, wherein a flip angle of the RF pulse is dynamically adjusted.

8. The magnetic resonance imaging apparatus of claim 1, wherein whether to perform the image acquisition in synchronism with a next biological signal is determined in accordance with a time required for current image acquisition and timing of the next biological signal estimated based on the temporal change in the patterns of the biological signal.

9. The magnetic resonance imaging apparatus of claim 8, wherein when it is determined that the image acquisition should be performed in synchronism with the next biological signal, the at least one image acquisition sequence condition parameter value is dynamically adjusted to be, at least one of a period between an application time of the labeling pulse and a first application time of the RF pulse, a flip angle of the labeling pulse, and a flip angle of the RF pulse.

10. The magnetic resonance imaging apparatus of claim 8, wherein when it is determined that the image acquisition should not be performed in synchronism with the next biological signal, subsequent image acquisition is performed in synchronism with a biological signal after one cycle.

11. The magnetic resonance imaging apparatus of claim 1, wherein whether to reject image data acquired in synchronism with a next biological signal is determined in accordance with a time required for current image data acquisition and timing of the next biological signal estimated based on the temporal change in the patterns of the biological signal.

12. The magnetic resonance imaging apparatus of claim 11, wherein when it is determined that the image data acquired in synchronism with the next biological signal should be rejected, the image acquisition condition is controlled to perform image data acquisition using a same encode pattern as an encode pattern used for the rejected image data.

13. The magnetic resonance imaging apparatus of claim 1, wherein the biological signal has a respiratory synchronization waveform, and when a cycle of the pattern of the biological signal is shorter than a predetermined cycle, the control unit controls at least a flip angle of the labeling pulse within a range of $90° \leq \alpha \leq 180°$.

14. The magnetic resonance imaging apparatus of claim 1, wherein the biological signal has a respiratory synchronization waveform.

15. The magnetic resonance imaging apparatus of claim 1, wherein the biological signal has an ECG waveform or a pulse waveform.

16. The magnetic resonance imaging apparatus of claim 1, wherein the temporal change in the patterns of the biological signal is temporal change in an interval of the biological signal.

17. The magnetic resonance imaging apparatus of claim 1, wherein the temporal change in the patterns of the biological signal is temporal change in a period of the biological signal.

18. The magnetic resonance imaging apparatus of claim 1, wherein the temporal change in the patterns of the biological signal is temporal change in wavelength of the biological signal.

* * * * *